US006934637B2

United States Patent
Murphey

(10) Patent No.: US 6,934,637 B2
(45) Date of Patent: Aug. 23, 2005

(54) METHOD FOR COMPARING AND CORRELATING ANALYSES OF CHANGES IN CELLS AND TISSUES

(76) Inventor: James P. Murphey, P.O. Box 356, Paradise, UT (US) 84328

( * ) Notice: Subject to any disclaimer, the term of this patent is extended or adjusted under 35 U.S.C. 154(b) by 0 days.

(21) Appl. No.: 10/423,808

(22) Filed: Apr. 25, 2003

(65) Prior Publication Data

US 2004/0215399 A1 Oct. 28, 2004

(51) Int. Cl.⁷ .............................................. G06F 19/00
(52) U.S. Cl. ........................................ 702/19; 382/133
(58) Field of Search ............................ 702/19; 600/569, 600/478, 475, 473; 436/63; 382/257, 133, 128

(56) References Cited

U.S. PATENT DOCUMENTS 6,143,512 A  * 11/2000  Markovic et al. ............. 435/21

* cited by examiner

Primary Examiner—John Barlow
Assistant Examiner—Stephen J. Cherry
(74) Attorney, Agent, or Firm—Fehr Law Firm; Thompson E. Fehr

(57) ABSTRACT

A method for comparing and correlating analyses of changes in cells and tissues wherein one or more analysts analyze features of medical importance in cytology specimens or surgical specimens to determine the degree of variation. A numeric or alphabetic scale is established, going from the least possible variation to the greatest possible variation of the feature. Using such a scale, each analyst assigns a number or letter to the degree of variation. These numbers or letters are displayed in specific locations along the first axis of an orthogonal system. Also displayed is a consensus degree of variation. The determination of one or more analysts is compared to the consensus degree of variation in order to determine, and assign an appropriate indicator based upon, the degree of accuracy. This may be done either visually or with a computer.

8 Claims, 3 Drawing Sheets

| TYPE | CN | DOS | MUI | L/R | SITE | DX | CAT |
|---|---|---|---|---|---|---|---|
| GYN | 03-2109 | 03/10/2003 | 54687 | N/A | CERVIX | D-5456 | 10 |
| GYN | 01-2324 | 03/12/2001 | 54687 | N/A | CERVIX | D-7777 | 20 |
| GYN | 98-1298 | 02/13/1998 | 54687 | N/A | CERVIX | D-6876 | 20 |
| GYN | 96-1434 | 02/15/1996 | 54687 | N/A | CERVIX | D-5456 | 10 |
| GYN | 94-0454 | 01/12/1994 | 54687 | N/A | CERVIX | D-3221 | 10 |
| GYN | 93-0045 | 01/01/1993 | 54687 | N/A | CERVIX | D-3221 | 10 |

| TYPE | CN | DOS | MUI | L/R | SITE | DX | CAT |
|------|------|------------|-------|-----|--------|--------|-----|
| GYN | 03-2109 | 03/10/2003 | 54687 | N/A | CERVIX | D-5456 | 10 |
| GYN | 01-2324 | 03/12/2001 | 54687 | N/A | CERVIX | D-7777 | 20 |
| GYN | 98-1298 | 02/13/1998 | 54687 | N/A | CERVIX | D-6876 | 20 |
| GYN | 96-1434 | 02/15/1996 | 54687 | N/A | CERVIX | D-5456 | 10 |
| GYN | 94-0454 | 01/12/1994 | 54687 | N/A | CERVIX | D-3221 | 10 |
| GYN | 93-0045 | 01/01/1993 | 54687 | N/A | CERVIX | D-3221 | 10 |

FIG. 1A

| TYPE | CASE | DOS | L/R | SITE | DX | IDX | R1 | R2 | R3 | R4 | R5 | FDX |
|---|---|---|---|---|---|---|---|---|---|---|---|---|
| SURG | S03-3245 | 09/03/2003 | N/A | CERVIX | D-5684 | 8 | 8 | | | | | 8 |
| GYN | C03-9999 | 08/15/2003 | N/A | CERVIX | D-5684 | 7 | 8 | | | | | 8 |
| GYN | C03-8776 | 05/29/2003 | N/A | CERVIX | D-3435 | 5 | 6 | | | | | 6 |
| GYN | C01-3487 | 03/08/2001 | N/A | CERVIX | D-2543 | 3 | 3 | | | | | 3 |
| GYN | C99-4512 | 04/14/1999 | N/A | CERVIX | D-2111 | 2 | 2 | | | | | 2 |
| GYN | C97-3456 | 03/23/1997 | N/A | CERVIX | D-2111 | 2 | 2 | | | | | 2 |
| GYN | C95-4886 | 04/16/1995 | N/A | CERVIX | D-2111 | 2 | 2 | | | | | 2 |

FIG. 2

METHOD FOR COMPARING AND CORRELATING ANALYSES OF CHANGES IN CELLS AND TISSUES

BACKGROUND OF THE INVENTION

1. Field of the Invention

This invention relates to a method for comparing and correlating analyses of changes in cells and tissues.

2. Description of the Related Art

U.S. Pat. No. 4,315,309 covers an Integrated Medical Test Data Storage and Retrieval System which produces written reports.

The inventor is, however, unaware of any such system which, after assigning numerical or alphabetical codes indicating a degree of change from normal, displays such changes for a given specimen along one axis of an orthogonal system while using the other axis to display such information chronologically for other specimens taken from the same body site of the same patient or organism.

BRIEF SUMMARY OF THE INVENTION

Either for human beings or for other living organisms, diseases and often abnormality or return to normality occur in stages. Identification of each stage is done by pathologists analyzing multiple cytology specimens or surgical biopsy specimens or both.

This process includes the customary steps of (1) acquiring a cytology specimen or a surgical tissue specimen or any other type of specimen to be evaluated, especially sequentially, for variations in features which can be assigned a level of abnormality or level of difference value or change (which all shall, for the purposes of this application, be included within the general term "degree of variation"); (2) preparing the specimen to make it suitable for evaluation, either by gross examination, microscopic examination, or other analytical method; and (3) analyzing features of medical importance (to the disease or abnormality) in the specimen to determine the degree of change, difference, or abnormality (degree of variation).

Also known for the process are the steps of (4) selecting a numeric or alphabetic scale to represent the full spectrum or a partial spectrum of possible changes in the features of medical importance and (5) assigning to the feature of interest in a specimen a number or letter indicating the degree of change, difference, or abnormality (degree of variation) within the scale.

A unique feature of a patent application of the present inventor filed concurrently with the present application is, however, displaying for a given specimen along a first axis, preferably a horizontal axis, of an orthogonal system, information for the specimen including the number or letter representing, for each of one or more of several analysts and preferably also for a consensus diagnosis, the degree of change, difference, or abnormality (degree of variation) for one or more features evaluated with each particular item of information being at a specified position along the first axis while also placing farther along a second axis, preferably a vertical axis, the same type of information for one or more additional specimens taken from the same body site of the same patient or organism with each particular item of information for the additional specimens being located at the same position along the first axis for the additional specimens as it was for the first specimen with the position along the vertical axis being arranged chronologically based upon the date a given specimen was obtained.

Of course, for convenience, each presentation of information along the first axis preferably includes information identifying the specimen.

The present invention establishes one or more ranges of difference between the consensus degree of variation and any analyst's degree of variation, uniquely identifies such range in terms of accuracy, compares an analyst's degree of variation with the consensus degree of variation, and assigns to the analyst's analysis the appropriate indication of accuracy.

BRIEF DESCRIPTION OF THE SEVERAL VIEWS OF THE DRAWING

FIG. 1A illustrates the left portion a preferred format of the display of the present invention to be used on a computer.

FIG. 2 portrays a preferred printed format of the display.

DETAILED DESCRIPTION OF THE INVENTION

Figure 1B:
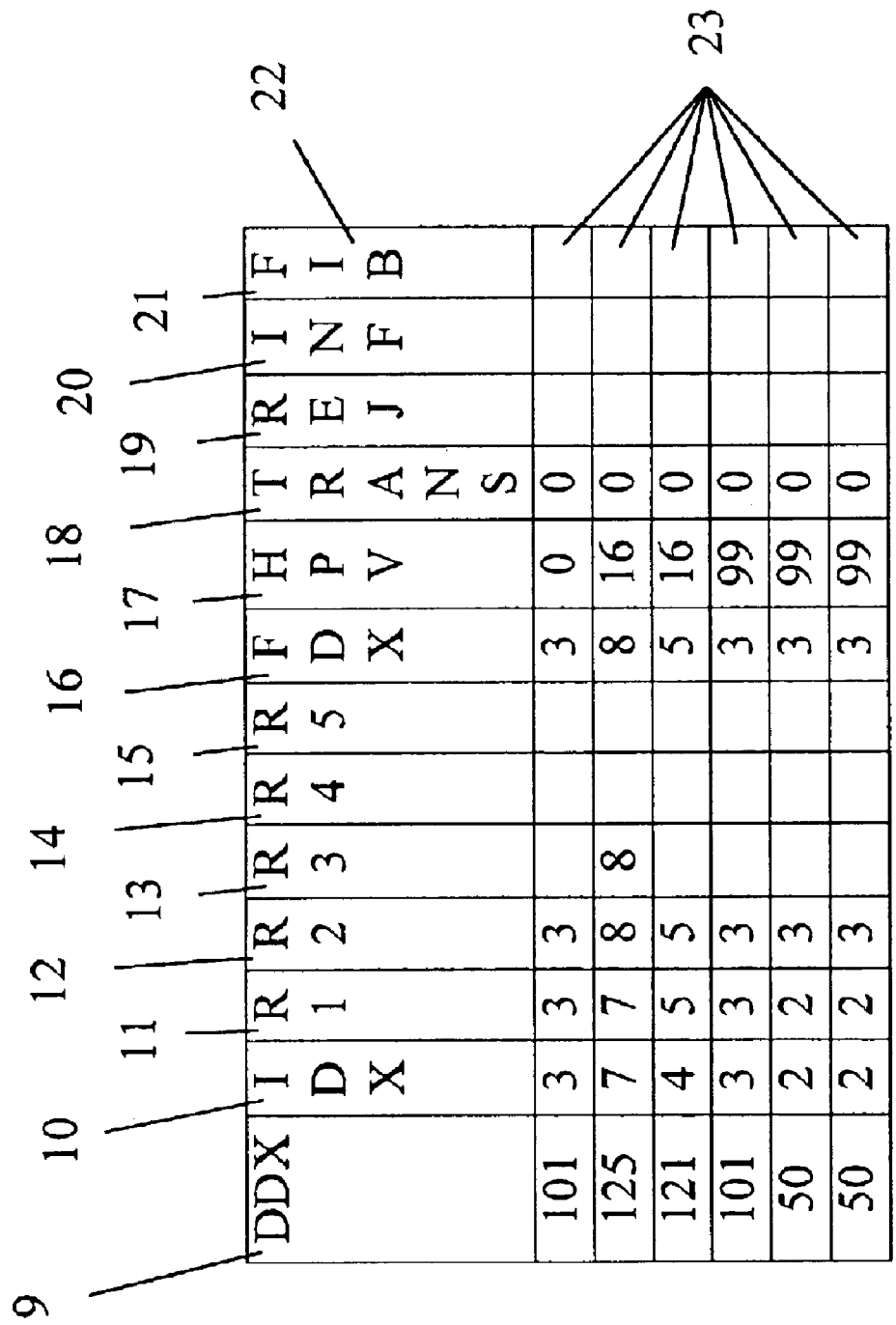
FIG. 1B shows the right portion of the display of FIG. 1A.

Physicians often utilize the terms "medicine" or "medical" to refer to the clinical diagnosis or treatment of disease, abnormality, or other damage to a human patient, meaning that such diagnosis or treatment is direct and intended primarily for correcting or curing the condition in the patient. This is often distinguished from such diagnosis or treatment primarily for the purpose of research.

For this patent application, however, the terms "medicine" or "medical" comprehend both clinical and research diagnosis or treatment of disease, abnormality, or other damage to a patient. Furthermore, although physicians and veterinarians usually distinguish between "medicine" and "veterinary medicine" or "medical" and "veterinary medical," the term "patient" in this patent application comprehends both human beings and other animals and, consequently, the terms "medicine" and "medical" include "veterinary medicine" and "veterinary medical," unless the context otherwise requires.

Although the terms "research" and "veterinary" or similar terms may occasionally be used in this patent application, such usage is for emphasis and should not be considered to limit the definitions provided above for "medicine," "medical," and "patient."

The present invention facilitates analyzing the quality of an analyst's evaluation of cytology and/or surgical biopsy specimens for features of medical importance. Most often such features indicate the presence or absence of pre-malignant or malignant changes, and most typically the present invention would be applied to sequential Pap smear and cervical biopsy diagnoses in human medicine.

When the analyst uses a new method for classifying and displaying which is the subject of a patent application of the present inventor filed concurrently with this application and which applies to many areas of medicine, including Pap smear cytology, non-Pap smear cytology, FNA cytology, and a variety of biopsies, such as liver biopsy, kidney biopsy, and bone marrow biopsy for inflammatory or neoplastic disease, the present invention may be utilized.

The method of classifying and displaying will first be explained.

In patients who might undergo organ transplant procedures, this method provides a means of serial assessment of features of medical interest in native organs prior to transplant, and in transplanted organs in the follow-up of such patients, including evaluation of transplant rejection.

The method of classifying and displaying under consideration may, additionally, be applied to other similar situations in veterinary medicine, or in research, in which the evaluation of any sequential cytology or surgical biopsy specimens take place. Progression or regression of abnormalities or pathologic processes may be identified.

The evaluation of abnormalities or pathological changes in cell and/or tissue specimens is generally the concern of the discipline of pathology. In the usual practice of pathology, methods for assessment of the status of a given organ system include evaluation of cell specimens, generally termed cytology specimens (usually obtained by scraping or the like), and evaluations of tissue biopsy or surgical resection specimens, generally termed surgical specimens, from various organs or parts of the body. These evaluations may be multiple and sequential from the same organ or body site and from the same patient; they may include a mix of cytology and surgical specimens and may also be taken from native or transplanted tissues or organs.

The comparison/correlation of results from evaluations of the various types of cytology and/or surgical specimens from the same organ system from the same patient may be extremely important for defining an abnormality or pathologic process and its progression or regression, to allow appropriate therapeutic intervention, or to avoid inappropriate therapeutic intervention. These considerations certainly apply to human specimens and also apply to specimens from non-human organisms such as wild, domestic, or research animals and organisms.

The sequential Papanicolaou smear (cytology) associated with uterine cervix biopsy (surgical) specimens may be used as the best example of a test system almost universally employed in human medicine, in which cytology and/or surgical biopsy material from the same organ system in the same patient is repeatedly and sequentially evaluated, and with which evolution of cell and/or tissue abnormalities may be detected. The most important changes to be identified with the Pap smear/cervical biopsy test system are those indicating evolution from normal or benign abnormal cell or tissue components to pre-malignant or malignant cell or tissue components. Cell changes within the spectrum from normal to pre-malignant to malignant, identified in the evaluation of such specimens, have been variously classified. The current most widely accepted classification scheme used in the United States is known as the Bethesda System. This system separates cell changes into a number of categories and descriptive diagnoses which are meaningful in that they reflect the biology of the most common pathway of evolution from benign to pre-malignant and malignant changes, and they allow appropriate diagnostic and therapeutic decision-making by an attending physician.

Optimal decision-making in the management of patients with Pap smear abnormalities requires analysis and correlation of the results of sequential Pap smears and biopsy procedures, and a knowledge of the import of the various diagnostic terms issued by a given analyst (pathologist or cytotechnologist or automated analyzer) or laboratory. The results of sequential Pap smears from a given patient must be correlated with one another and with the results of any cervical biopsy procedure for a given patient by any cytology laboratory applying for accreditation and licensure. Also required is the correlation of non-Pap smear cytology results with any related tissue biopsy material. Such correlations may be virtually impossible without the use of a computerized information retrieval and processing system; and, even with computerized records, the identification, correlation, and analysis of results from all specimens of related type may be cumbersome and time consuming. Efficient laboratory management and cost-effective medical practice require a simple and rapid results review and correlation method to allow processing of the large volumes of data generated by test systems of this type.

The sequential sampling of cell material and/or tissue biopsy specimens is not limited to the Pap smear/biopsy test system described above, but is common to many situations in human medicine. For example, patients who receive a transplant bone marrow, liver, kidney, heart, etc. may undergo sequential biopsy procedures of the native organ prior to transplant and will likely undergo sequential surgical biopsy procedures of the transplanted organ during the course of their treatment.

Using the Pap smear/uterine biopsy system as an example for illustration of a method of classification is, though, appropriate.

In the application of the numeric categorization scheme to Pap smear specimens, the Bethesda classification scheme may be generally transcribed into the following range of numbers:

1=unsatisfactory specimen
2=within normal limits
3=inflammatory/reactive change
4=atypical cells, benign/benign neoplasm
5=atypical cells of uncertain significance, not otherwise specified
6=atypical cells of uncertain significance, possibly pre-malignant/rule out high-grade intraepithelial lesion
7=low-grade intraepithelial lesion
8=high-grade intraepithelial lesion
9=atypical cells suspicious for invasive tumor
10=invasive tumor These same numeric values can be assigned to biopsy specimen results, where:

1=unsatisfactory specimen
2=within normal limits
3=inflammatory/reactive change
4=atypical but benign cellular proliferation, benign neoplasm
5=atypia of uncertain significance, not otherwise specified
6=atypia of uncertain significance, possibly pre-malignant
7=low-grade intraepithelial lesion
8=high-grade intraepithelial lesion
9=atypical cells suspicious for malignant (invasive) tumor
10=malignant (invasive) tumor When a Pap smear or surgical specimen result is listed for a given patient in accordance with the method of classifying and displaying under consideration, the value indicating the level of abnormality (level of variation) along with all necessary associated information is preferably written as a series of items of information in one horizontal line. When sequential Pap smear and biopsy results for a given patient are listed in order of the date of sampling, they would appear as a series of such single lines of information in the display, and the list which is thereby generated may be displayed with the most remote sampling at the bottom of the list proceeding chronologically to the most recent sampling at the top of the list or vice-versa.

A list of specimens of this type from a given patient, in accordance with the the method of classifying and displaying under consideration, preferably includes columns labeled with the name of the feature assessed, with a number from the preceding spectrum of values indicating the degree of abnormality (degree of variation) for that feature. The numeric values for degree of abnormality (degree of variation) will, thus, be arrayed in a vertical column. This format gives the analyst the opportunity to detect at a glance any significant abnormality (variation) in the history of the patient in question and to trace the evolution of that abnormality (variation).

Within the same line and column format the review of any given specimen by another analyst is optionally recorded as an item of information in the horizontal line containing all other pertinent information for that specimen.

Difficult diagnostic problems in the evaluation of cell and/or biopsy material are commonly reviewed by a second or by several other pathologists, and the results of those additional evaluations may be important in the development of a definitive and final diagnosis. Within the display format those review diagnoses are preferably listed in sequence adjacent to the initial diagnosis. A final consensus diagnosis is preferably listed adjacent to the review diagnoses.

In this format, the entire patient history is displayed from bottom to top of the list of specimens, and the entire specimen history for each specimen is displayed from the left to the right side of each information line. This format, therefore, allows essentially total knowledge of the patient and specimen history to be learned at a glance.

The values and categories used in the preceding example represent only one application of the present invention to a particular system. For example, many other numeric or alphabetic ranges and categories of abnormality (variation) might be utilized depending upon the specimen, disease process, organ system to be evaluated, type of organism, variables involved, etc.

As an example of the application of this method to the evaluation of other types of human specimens, any cytology specimen result (e.g., those from fine needle aspiration biopsy specimens) can be assigned the same or a similar numeric or alphabetic value and listed within a patient history as above, along with results from surgical specimen examinations from the same source. Correlations between FNA cytology results and surgical biopsy or resection specimen results are then easily done within the format of the display.

The application of the numeric categorization system to liver biopsy specimen results analysis can be done by assigning a range of values to medically important features identified in liver biopsy material, such as degree of inflammation and degree of fibrosis, as follows:

0=no inflammation
1=mild inflammation
2=moderate inflammation
3=moderately severe inflammation
4=severe inflammation
0=no fibrosis
1=portal fibrosis
2=portal and periportal fibrosis
3=septal, periportal and portal fibrosis
4=cirrhosis A list of specimens of this type from a given patient would include columns labeled with the name of the feature assessed, with a number from the above spectrum of values indicating the degree of abnormality (degree of variation) for that feature, for sequential biopsy results. Native or transplant liver biopsy results are optionally included, and the results columns are preferably arranged toward the right side of the display, making the evolution of changes (variations) in the various categories obvious at a glance. When coupled with a diagnostic category defining the etiology of the hepatic inflammatory process, the preceding could be used to trace the evolution toward end-stage liver disease in all patients with a particular type of liver disease, e.g., hepatitis C viral hepatitis.

Essentially, as indicated above, the present invention comprises assigning to features of medical importance (to a disease or abnormality) in a specimen numbers or letters selected from a scale of consecutive numbers or letters representing the full spectrum or a partial spectrum of possible changes (variations) in such features wherein the number or letter indicates the degree of change, difference, or abnormality (degree of variation) of the feature within the scale and then displaying the information for such specimen as described below.

The preferred display includes one or more specimen history lines arranged vertically to create the patient history list. (Of course, as indicated in the Brief Summary of the Invention, the orientation can be such that each specimen history line is a vertical line; and different specimen history lines can be arranged horizontally with respect to one another.)

The specimen history line includes information items listed in sequence, in separated areas which may represent data fields, and which, when multiple specimen history lines are stacked to form the patient history list, form a vertical column in that list, so that each information item is located above that item of the same type in the next entry in the series of specimen history lines which form the patient history list. The level of abnormality (variation) value appears as a number or letter (Of course, consistency must be maintained in using solely numbers or solely letters for a given type of information.) in a vertical column which allows rapid recognition of significant changes in that number in a series of specimen evaluations. Within the specimen history line optionally appears the level of abnormality (variation) assigned to a particular feature by more than one analyst and also any final, summary, or consensus (generally termed "consensus" for this patent application) value for the level of abnormality (variation) for that feature. Then each specimen history line contains all information resulting from sequential evaluations by one analyst or a multiplicity of evaluations by several analysts of the specimen in question. The specimen history line may also include a number or letter representing the level of abnormality for more than one characteristic or feature of the specimen evaluated. Preferably, each column in the patient history list is labeled to allow instant recognition of the feature of medical importance, or nature of the information, to which the column applies.

FIG. 1A and FIG. 1B illustrate a preferred embodiment of the display for a computer. Columns preferably are for specimen type 1; case number 2; date of diagnostic procedure 3; system patient unique identifier 4; side of origin 5 if from a bilateral organ structure; specimen source/site 6; diagnosis 7; diagnosis category 8; descriptive diagnosis 9; numeric value for level of abnormality (variation) for features of medical interest assigned by the initial analyst 10; numeric value for level of abnormality (variation) for features of medical interest assigned by other reviewing analysts, if any 11 through 15; a final (consensus) abnormality (variation) value 16 (The consensus value is by default the value assigned by the initial analyst for cases not subjected to any review; for cases reviewed one or more times, the consensus abnormality (variation) value is derived from the assessment of all review values (diagnoses) and usually represents a consensus opinion.), human papilloma virus genotype 17 (which is a number between 0 and 99), native or transplant organ 18, rejection score 19, degree of inflammation 20, and degree of fibrosis 21.

Of course, in the figure, the first row 22 is used to label the columns; and the remaining rows 23 represent different specimens.

Preferably, the information for native or transplant organ 18 is 0 for a native organ, 1 for a first transplant organ, 2 for a second transplant organ, etc.

The rejections score is preferably a number between 0 and 16 derived from the degree of transplant infiltrate, extent of same, amount of necrosis, etc.; and empty box indicates that no score has been generated.

As indicated above, with respect to the display the generalized present invention comprises displaying for a given specimen along a first axis, preferably a horizontal axis, of an orthogonal system information for the specimen including the number or letter representing, for each of one or more of several analysts and preferably also for a consensus diagnosis, the degree of change, difference, or abnormality (degree of variation) for one or more features evaluated with each particular item of information being at a specified position along the first axis while also placing farther along a second axis, preferably a vertical axis, the same type of information for one or more additional specimens taken from the same body site of the same patient or organism with each particular item of information for the additional specimens being located at the same position along the first axis for the additional specimens as it was for the first specimen with the position along the vertical axis being arranged chronologically based upon the date a given specimen was obtained.

The display may be generated from a computer based upon data input into the computer or by other means, such as by hand or by a typewriter. The display may be on paper or on a computer display.

When the display is on paper, the preferred format is that shown in FIG. 2. (The specific illustrative example shown constitutes a high-grade PAP smear report.)

If desired, either on paper or on a computer display (but especially when paper is utilized), when a number of specimens have been taken from a number of patients, the display may be done for each of several patients with one or more identifying indicia for each patient, such as the patient's name and Social Security number, preceding the information for that patient.

The present invention involves viewing the consensus degree of variation and the degree of variation determined by any analyst. The difference between these degrees of variation is then found. One or more ranges of difference between the consensus degree of variation and the degree of variation determined by an analyst are established and uniquely identified to indicate levels of accuracy in the analysis. For example, when a scale of 1 to 10 (for convenience and clarity, whether letters or numbers are utilized, each will be considered to be a unit; so, for example, 8 will be within 2 units of 6 and D will be within two units of B) is utilized, if the degree of variation of the analyst is within one unit (numbers, in the present example) of the consensus, the analyst's analysis is identified as having no significant discrepancy; if it is two units different from the consensus, the analyst's analysis is identified as having a minor discrepancy; and if the difference is three units or greater, the analyst's analysis (or determination) is identified as having a major discrepancy.

The viewing, assignment of accuracy, and recording of results may be done by an individual or by a computer. Of course, "viewing" by a computer would be accessing the degrees of variation that had been input into a computer's memory.

As used herein the term "preferable" or "preferably" means that a specified element or technique is more acceptable than another but not that such specified element or technique is a necessity.

I claim:

1. A method for comparing analyses of changes in cells and tissues of a specimen, which comprises:

viewing a number or letter representing a degree of variation for a feature of medical interest in a specimen determined by an analyst and a number or letter representing a consensus degree of variation for such feature in the specimen, wherein such number or letter is selected from a scale of consecutive numbers or letters representing the spectrum of possible variations in such feature and wherein the number or letter is used to indicate a degree of variation of the feature within the scale and wherein such numbers or letters lie along an axis of an orthogonal system;

comparing the letter or number representing the degree of variation assigned by the analyst with the number or letter of the consensus degree of variation;

setting criteria for accuracy based upon one or more ranges of difference between the letter or number representing the degree of variation assigned by the analyst and the number or letter of the consensus degree of variation;

assigning a unique identifier to each such range; and indicating the identifier applicable to the range within which the difference between the degree of variation assigned by the analyst and the number or letter of the consensus degree of variation lies.

2. The method for comparing analyses of changes in cells and tissues of a specimen as recited in claim 1, wherein:

when, using a scale of 1 to 10, the degree of variation of the analyst is within 1 unit of the consensus degree of variation, the analyst's determination is identified as having no significant discrepancy;

when, using a scale of 1 to 10, the degree of variation of the analyst is 2 units different from the consensus degree of variation, the analyst's determination is identified as having a minor discrepancy; and when, using a scale of 1 to 10, the degree of variation of the analyst is 3 or more units different from the consensus degree of variation, the analyst's determination is identified as having a major discrepancy.

3. A method for comparing analyses of changes in cells and tissues of a specimen, which comprises:

viewing a number representing a degree of variation for a feature of medical interest in a specimen determined by an analyst and a number representing a consensus degree of variation for such feature in the specimen, wherein such number is selected from a scale of consecutive numbers representing the spectrum of possible variations in such feature and wherein the number is used to indicate a degree of variation of the feature within the scale and wherein such numbers lie along an axis of an orthogonal system;

comparing the number representing the degree of variation assigned by the analyst with the number of the consensus degree of variation;

setting criteria for accuracy based upon one or more ranges of difference between the number representing the degree of variation assigned by the analyst and the number of the consensus degree of variation;

assigning a unique identifier to each such range; and indicating the identifier applicable to the range within which the difference between the degree of variation assigned by the analyst and the number of the consensus degree of variation lies.

4. The method for comparing analyses of changes in cells and tissues of a specimen as recited in claim 3, wherein:

when, using a scale of 1 to 10, the degree of variation of the analyst is within 1 unit of the consensus degree of variation, the analyst's determination is identified as having no significant discrepancy;

when, using a scale of 1 to 10, the degree of variation of the analyst is 2 units different from the consensus degree of variation, the analyst's determination is identified as having a minor discrepancy; and when, using a scale of 1 to 10, the degree of variation of the analyst is 3 or more units different from the consensus degree of variation, the analyst's determination is identified as having a major discrepancy.

5. A method for comparing analyses of changes in cells and tissues of a specimen, which comprises:

accessing by computer a number or letter representing a degree of variation for a feature of medical interest in a specimen determined by an analyst and stored in the memory of the computer and a number or letter representing a consensus degree of variation for such feature in the specimen and stored in the computer, wherein such number or letter is selected from a scale of consecutive numbers or letters representing the spectrum of possible variations in such feature and wherein the number or letter is used to indicate a degree of variation of the feature within the scale and wherein such numbers or letters lie along an axis of an orthogonal system;

comparing, using the computer, the letter or number representing the degree of variation assigned by the analyst with the number or letter of the consensus degree of variation;

setting criteria for accuracy based upon one or more ranges of difference between the letter or number representing the degree of variation assigned by the analyst and the number or letter of the consensus degree of variation;

storing such criteria in the memory of the computer;

assigning a unique identifier to each such range;

storing such unique identifiers in the memory of the computer; and having the computer indicate the identifier applicable to the range within which the difference between the degree of variation assigned by the analyst and the number or letter of the consensus degree of variation lies.

6. The method for comparing analyses of changes in cells and tissues of a specimen as recited in claim 5, wherein:

when, using a scale of 1 to 10, the degree of variation of the analyst is within 1 unit of the consensus degree of variation, the analyst's determination is identified as having no significant discrepancy;

when, using a scale of 1 to 10, the degree of variation of the analyst is 2 units different from the consensus degree of variation, the analyst's determination is identified as having a minor discrepancy; and when, using a scale of 1 to 10, the degree of variation of the analyst is 3 or more units different from the consensus degree of variation, the analyst's determination is identified as having a major discrepancy.

7. A method for comparing analyses of changes in cells and tissues of a specimen, which comprises:

accessing by computer a number representing a degree of variation for a feature of medical interest in a specimen determined by an analyst and stored in the memory of the computer and a number representing a consensus degree of variation for such feature in the specimen and stored in the computer, wherein such number is selected from a scale of consecutive numbers representing the spectrum of possible variations in such feature and wherein the number is used to indicate a degree of variation of the feature within the scale and wherein such numbers lie along an axis of an orthogonal system;

comparing, using the computer, the number representing the degree of variation assigned by the analyst with the number of the consensus degree of variation;

setting criteria for accuracy based upon one or more ranges of difference between the number representing the degree of variation assigned by the analyst and the number of the consensus degree of variation;

storing such criteria in the memory of the computer;

assigning a unique identifier to each such range;

storing such unique identifiers in the memory of the computer; and having the computer indicate the identifier applicable to the range within which the difference between the degree of variation assigned by the analyst and the number of the consensus degree of variation lies.

8. The method for comparing analyses of changes in cells and tissues of a specimen as recited in claim 7, wherein:

when, using a scale of 1 to 10, the degree of variation of the analyst is within 1 unit of the consensus degree of variation, the analyst's determination is identified as having no significant discrepancy;

when, using a scale of 1 to 10, the degree of variation of the analyst is 2 units different from the consensus degree of variation, the analyst's determination is identified as having a minor discrepancy; and when, using a scale of 1 to 10, the degree of variation of the analyst is 3 or more units different from the consensus degree of variation, the analyst's determination is identified as having a major discrepancy.

* * * * *